US006472587B1

(12) United States Patent
Lerchl et al.

(10) Patent No.: US 6,472,587 B1
(45) Date of Patent: Oct. 29, 2002

(54) PRODUCTION OF A 5-(2-CHLORO-4-(TRIFLUOROMETHYL)PHENOXY)-2-NITROBENZOIC ACID OR 7-CHLORO-3-METHYLLQUINOLINE-8-CARBOXYLIC ACID-TOLERANT PLANT BY EXPRESSING AN EXOGENOUS 5-(2-CHLORO-4-(TRIFLUOROMETHYL)PHENOXY)-2-NITROBENZOIC ACID OR 7-CHLORO-3-METHYLLQUINOLINE-8-CARBOXYLIC ACID-BINDING ANTIBODY IN THE PLANT

(75) Inventors: Jens Lerchl, Ladenburg; Achim Möller, Grünstadt; Ralf-Michael Schmidt, Kirrweiler; Helmut Schiffer, Mutterstadt; Udo Rabe, Dannstadt-Schauernheim; Udo Conrad, Gatersleben, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/381,464

(22) PCT Filed: Mar. 24, 1998

(86) PCT No.: PCT/EP98/01731

§ 371 (c)(1),
(2), (4) Date: Sep. 21, 1999

(87) PCT Pub. No.: WO98/42852

PCT Pub. Date: Oct. 1, 1998

(30) Foreign Application Priority Data

Mar. 25, 1997 (DE) .......................... 197 12 507

(51) Int. Cl.$^7$ .............................. A01H 5/00; A01H 1/02; C12N 15/82; C12N 15/84; C12N 15/13
(52) U.S. Cl. ...................... 800/300; 800/288; 800/287; 800/292; 800/293; 800/294; 800/317.3; 435/320.1; 435/468; 435/469; 435/470; 435/418; 435/419; 435/414; 435/421; 536/23.53; 536/23.4
(58) Field of Search .............................. 536/23.1, 23.53, 536/23.4; 435/468, 469, 470, 410, 419, 418, 320.1, 414; 530/387.1, 387.3, 388.9; 800/278, 287, 288, 292, 293, 294, 300, 317.3

(56) References Cited

U.S. PATENT DOCUMENTS 5,162,602 A   11/1992   Somers et al. ........... 800/300.1
5,290,696 A    3/1994   Somers et al. .............. 435/424
5,858,920 A    1/1999   Dahmen .................... 504/244

FOREIGN PATENT DOCUMENTS

| EP | 0284 419 A1 | 9/1988 |
| EP | 0520 962 A2 | 12/1992 |
| EP | 0716 808 A2 | 6/1996 |
| WO | 87/05629 | 9/1987 |
| WO | 92/04449 | 3/1992 |
| WO | 94/23018 | 10/1994 |
| WO | 96/38567 | 12/1996 |
| WO | 97/04088 | 2/1997 |

OTHER PUBLICATIONS

Yuan, L. et al., "Modification of plant components." 1997, Current Opinion in Biotechnology, vol. 8, pp. 227–233.*
Sharp et al., *ACS Symposium Series 446*, "Development of Highly Specific Antibodies to Alachlor by Use of a Carboxy–Alachlor Protein Conjugate," Chapter 10, Jan. 21–25, 1990, pp. 87–95.
Hiatt et al., *Nature*, "Production of antibodies in transgenic plants," vol. 342, Nov. 2, 1989, pp. 76–78.
Ma et al., *Annals of the New York Academy of Sciences*, "Antibody Production and Engineering in Plants," vol. 792, 1996, pp. 72–81.
Artsaenko et al., *The Plant Journal*, "Expression of a single–chain Fv antibody against abscisic acid creates a wilty phenotype in transgenic tobacco," vol. 8, No. 5, 1995, pp. 745–750.
Asboth et al., Abst. No. XP–002074579, "Catalytically active monoclonal antibodies for herbicide–resistant crop plant production," (conference paper), 1991, p. 21, Hungary.
Swain, *Trends in Biotechnology*, "Antibodies in Plants,", vol. 9, No. 4, Apr. 9, 1991, pp. 107–109.
Bell et al., *Gene*, "Sequences of the cDNAs encoding the heavy– and light–chain Fab region of an antibody to the phenylurea herbicide diuron," vol. 165, 1995, pp. 323–324.
Fiedler et al., *Biotechnology*, "High–Level Production and Long–Term Storage of Engineered Antibodies in Transgenic Tobacco Seeds," vol. 13, Oct. 1995, pp. 1090–1093.
Hiatt et al., *Books in Soils and Plants and the Environment: Transgenic Plants: Fundamentals and Applications*, "Assembly of Multimeric Proteins in Plants Cells: Characteristics and Uses of Plant–Derived Antibodies," Jan. 1993, pp. 221–237.
Schouten et al., *Plant Molecular Biology*, "The C–terminal KDEL sequence increases the expression level of a single–chain antibody designed to be targeted to both the cytosol and the secretory pathway in transgenic tobacco," vol. 30, 1996, pp. 781–793.

* cited by examiner

*Primary Examiner*—David T. Fox
*Assistant Examiner*—David H Kruse
(74) *Attorney, Agent, or Firm*—Keil & Weinkauf

(57) ABSTRACT

Process for production of herbicide-tolerant plants by expressing an exogenous herbicide-binding polypeptide in plants or plant organs. The invention furthermore relates to the use of the corresponding nucleic acids which encode a polypeptide, an antibody or parts of an antibody with herbicide-binding properties in transgenic plants, and the thus transformed plant itself.

24 Claims, 3 Drawing Sheets

US 6,472,587 B1

Figure 1:
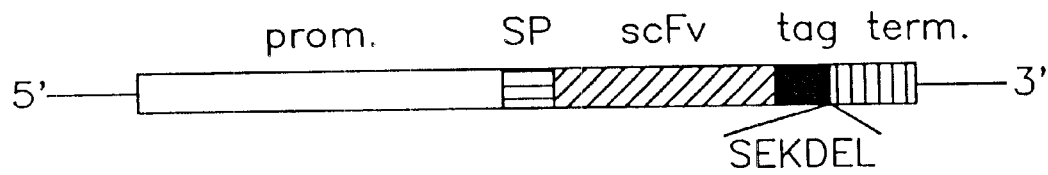

PRODUCTION OF A 5-(2-CHLORO-4-(TRIFLUOROMETHYL)PHENOXY)-2-NITROBENZOIC ACID OR 7-CHLORO-3-METHYLLQUINOLINE-8-CARBOXYLIC ACID-TOLERANT PLANT BY EXPRESSING AN EXOGENOUS 5-(2-CHLORO-4-(TRIFLUOROMETHYL)PHENOXY)-2-NITROBENZOIC ACID OR 7-CHLORO-3-METHYLLQUINOLINE-8-CARBOXYLIC ACID-BINDING ANTIBODY IN THE PLANT

BACKGROUND OF THE INVENTION

1. Field of the Invention

The present invention relates to a process for the production of herbicide-tolerant plants by expressing an exogenous herbicide-binding polypeptide in plants or plant organs. The invention furthermore relates to the use of the corresponding nucleic acids which encode a polypeptide, an antibody or parts of an antibody with herbicide-binding properties in transgenic plants, and the thus transformed plant itself.

2. Description of the Related Art

It is known that genetic engineering methods allow the specific transfer of foreign genes into the genome of a plant. This process is termed transformation, and the resulting plants transgenic plants. Transgenic plants are currently being employed in various fields of biotechnology. Examples of insect-resistant plants (Vaek et al. Plant Cell 5 (1987), 159–169), virus-resistant plants (Powell et al. Science 232 (1986), 738–743) and ozone-resistant plants (van Camp et al. BioTech. 12 (1994), 165–168). Examples of improved quality characteristics achieved by genetic engineering are: improved shelf life of fruit (Oeller et al. Science 254 (1991), 437–439), increased starch production in potato tubers (Stark et al. Science 242 (1992), 419), changes in starch (Visser et al. Mol. Gen. Genet. 225 (1991), 289–296) and lipid composition (Voelker et al. Science 257 (1992), 72–74), and production of foreign polymers (Poirer et al. Science 256 (1992), 520–523).

An important target of work carried out in the field of plant molecular genetics is the generation of herbicide tolerance. Herbicide tolerance is characterized by an improved compatibility (in terms of type or level) of the plant or plant organs with the herbicide applied. This can be effected in various ways. The known methods are utilization of a metabolic gene, for example the pat gene, in connection with glufosinate resistance (WO 8705629) or a target enzyme which is resistant to the herbicide, such as in the case of enolpyruvyl shikimate-3-phosphate synthase (WO 9204449), which is resistant to glyphosate, and the use of a herbicide in cell and tissue culture for the selection of tolerant plant cells and resulting resistant plants, such as described in the case of acetyl-CoA-carboxylase inhibitors (U.S. Pat. No. 5,162,602, U.S. Pat. No. 5,290,696).

Antibodies are proteins as component of the immune system. A joint feature of all antibodies is their spatial, globular structure, the construction of light and heavy chain and their basic capability of binding molecules or parts of a molecular structure with high specificity (Alberts et al., in: Molekularbiologie der Zelle [Molecular Biology of the Cell], 2nd Edition 1990, VCH Verlag, ISBN 3-527-27983-0, 1198–1237). On the basis of these properties, antibodies have been utilized for a number of tasks. Application can be divided into application of the antibodies within the animal and human organisms in which they are produced, that is to say the so-called in-situ applications, and the ex-situ applications, ie. utilization of the antibodies after they have been isolated from the producing cells or organisms (Whitelam und Cockburn, TIPS Vol.1, 8 (1996), 268–272).

The use of somatic hybrid cell lines (hybridomas) as a source of antibodies against very specific antigens is based on work carried out by Köhler and Milstein (Nature 256 (1975) 495–97). This process allows so-called monoclonal antibodies to be produced which have a uniform structure and which are produced by means of cell fusion. Spleen cells of an immunized mouse are fused with mouse myeloma cells. This gives hybridoma cells which proliferate infinitely. At the same time, the cells secrete specific antibodies against the antigen with which the mouse had been immunized. The spleen cells provide the capability of antibody production while the myeloma cells contribute the capacity of unlimited growth and continuous secretion of antibodies. Since each hybridoma cell, being a clone, is derived from a single B cell, all antibody molecules produced have the same structure, including the antigen binding site. This method has greatly promoted the use of antibodies since antibodies which have a single, known specificity and a homogeneous structure are now available in unlimited quantities. Monoclonal antibodies are used widely in immunodiagnostics and as therapeutics.

In recent years, the so-called phage display method has become available for the production of antibodies, and here the immune system and the various immunizations in the animal are avoided. The affinity and specificity of the antibody are made to measure in vitro (Winter et al., Ann. Rev. Immunol. 12 (1994), 433–455; Hoogenboom TIBTech Vol 15 (1997), 62–70). Gene segments which contain the sequence which encodes the variable region of antibodies, ie. the antigen binding site, are fused with genes for the coat protein of a bacteriophage. Then, bacteria are infected with phages which contain such fusion genes. The resulting phage particles are now equipped with coats containing the antibody-like fusion protein, the antibody-binding domain pointing outward. Such a phage display library can now be used for isolating the phage which contains the desired antibody fragment and which binds specifically to a certain antigen. Each phage isolated in this manner produces a monoclonal antigen-binding polypeptide which corresponds to a monoclonal antibody. The genes for the antigen binding site, which are unique for each phage, can be isolated from the phage DNA and employed for constructing complete antibody genes.

In the field of crop protection, antibodies were utilized in particular as analytical tools ex-situ for the qualitative and quantitative detection of antigens. This includes the detection of plant constituents, herbicides or fungicides in drinking water (Sharp et al. (1991) ACS Symp Ser., 446 (Pestic. Residues Food Saf.) 87–95), soil samples (WO 9423018) or in plants or plant organs, and the utilization of antibodies as auxiliaries for the purification of bound molecules.

The production of immunoglobulins in plants was first described by Hiatt et al., Nature, 342 (1989), 76–78. The spectrum encompasses single-chain antibodies up to multimeric secretory antibodies (J. Ma and Mich Hein, 1996, Annuals New York Academy of Sciences, 72–81).

More recent attempts utilize antibodies in-situ for defending plants against pathogens, in particular viral diseases, by expressing, in plant cells, specific antibodies or parts thereof which are directed against viral coat proteins (Tavladoraki et al., Nature 366 (1993), 469–472; Voss et al., Mol. Breeding 1 (1995), 39–50).

An analogous approach has also been utilized for defending the plant against infection by nematodes (Rosso et al., Biochem Biophys Res Com, 220 (1996) 255–263). There exist examples for an application in pharmacology where the in-situ expression of antibodies in plants is utilized for oral immunization (Ma et al., Science 268 (1995), 716–719; Mason and Arntzen, Tibtech Vol 13 (1996), 388–392). The body is provided with antibodies formed by the plant and originating from plants or plant organs which are suitable for consumption, via the mouth, throat or digestive tract, which antibodies cause efficient immunoprotection. Moreover, a single-chain antibody against the low-molecular-weight plant hormone abscisic acid has already been expressed in plants, and a reduced availability of plant hormones, due to binding of abscisic acid in the plant, has been observed (Artsaenko et al., The Plant Journal 8 (5) (1995) 754–750).

Chemical control of weeds in agronomically important crops requires the use of highly selective herbicides. However, in some cases it is difficult to develop sufficiently selective herbicides which do not cause damage of the plant which provides the yield in any crop. The introduction of herbicide-resistant or -tolerant crop plants can contribute to solving this problem.

The development of herbicide-resistant crop plants by tissue culture or seed mutagenesis and natural selection is limited. Only those plants can be manipulated via tissue culture techniques where entire plants can be regenerated successfully from cell cultures. Moreover, following mutagenesis and selection, crop plants may display undesirable characteristics which have to be reeliminated by, in some cases repeated, back-crossing. Also, the introduction of a resistance by performing crosses would be restricted to plants of the same species.

It is for the abovementioned reasons that the genetic engineering approach of isolating a resistance-encoding gene and transferring it into crop plants in a targeted manner is superior to the traditional plant breeding method.

To date, the development of herbicide-tolerant or herbicide-resistant crop plants, by molecular biology methods, requires a knowledge of the mechanism of action of the herbicide in the plant and also that genes which impart resistance to the herbicide can be found. A large number of herbicides which are presently utilized commercially act by blocking an enzyme of an essential amino acid, lipid or pigment biosynthesis step. Herbicide tolerance can be generated by altering the genes of these enzymes in such a way that the herbicide can no longer be bound and by introducing these altered genes into crop plants. An alternative example is to find analogous enzymes in nature, for example in microorganisms which exhibit a natural resistance to the herbicide. This resistance-imparting gene is isolated from such a microorganism, recloned into suitable vectors and subsequently, after successful transformation, expressed in herbicide-sensitive crop plants (WO 96/38567).

BRIEF SUMMARY OF THE INVENTION

It was an object of the present invention to develop a novel, generally utilizable genetic engineering method for producing herbicide-tolerant transgenic plants.

We have found that this object is achieved, surprisingly, by a process of expressing, in the plants, an exogenous polypeptide, antibody or parts of an antibody with herbicide-binding properties.

DETAILED DESCRIPTION OF THE INVENTION

The present invention relates firstly to the production of a herbicide-binding antibody and the cloning of the relevant gene or gene fragment.

The first step is to produce a suitable antibody which binds the herbicide. This can be effected, inter alia, by immunizing a vertebrate, in most cases mouse, rat, dog, horse, donkey or goat, with an antigen. The antigen in this case is a fungicidally active compound which is associated or coupled to a higher-molecular-weight carrier such as bovine serum albumin (BSA), chicken ovalbumin, keyhole limpet hemocyanine (KLH) or other carriers, via a functional group. After antigen has been applied repeatedly, the immune response is monitored with customary methods, and a suitable antiserum is thus isolated. Initially, this approach yields a polyclonal serum which contains antibodies with differing specificities. For the targeted in-situ use, it is necessary to isolate the gene sequence which encodes a single, specific, monoclonal antibody. A variety of routes are available for this purpose. The first approach exploits the fusion of antibody-producing cells and cancer cells to give a hybridoma cell culture which continuously produces antibodies and which finally, by singling the clones obtained, leads to a homogeneous cell line which produces a defined monoclonal antibody.

The cDNA for the antibody, or parts of the antibody, viz. the so-called single chain antibody (scFv), is isolated from such a monoclonal cell line. These cDNA sequences can then be cloned into expression cassettes and used for the functional expression in prokaryotic and eukaryotic organisms, including plants.

Alternatively, it is possible to select antibodies via phage display libraries, and these antibodies bind herbicide molecules and convert them catalytically into a product which has non-fungicidal properties. Methods for raising catalytic antibodies are described in Janda et al., Science 275 (1997) 945–948, Chemical selection for catalysis in combinatorial Antibody libraries; Catalytic Antibodies, 1991, Ciba Foundation Symposium 159, Wiley-Interscience Publication. Cloning the gene of this catalytic antibody and expressing it in a plant may, in principle, also lead to a herbicide-resistant plant.

The invention particularly relates to expression cassettes whose encoding sequence encodes a herbicide-binding polypeptide or a functional equivalent thereof, and to the use of these expression cassettes for the production of a herbicide-tolerant plant. The nucleic acid sequence can be, for example, a DNA sequence or a cDNA sequence. Encoding sequences which are suitable for insertion into an expression cassette according to the invention are, for example, those which contain a DNA sequence from a hybridoma cell which encodes a polypeptide with herbicide-binding properties and thus impart resistance to plant-enzyme inhibitors to the host.

Moreover, the expression cassettes according to the invention contain regulatory nucleic acid sequences which govern expression of the encoding sequence in the host cell. In a preferred embodiment, an expression cassette according to the invention comprises upstream, ie. on the 5'-end of the encoding sequence, a promoter and downstream, ie. on the 3'-end, a polyadenylation signal and, if appropriate, other regulatory elements which are linked operatively with the in-between encoding sequence for the polypeptide with herbicide-binding properties and/or transit peptide. Operative linkage is to be understood as meaning the sequential arrangement of promoter, encoding sequence, terminator and, if appropriate, other regulatory elements in such a way that each of the regulatory elements can function as intended when the encoding sequence is expressed. The sequences preferred for operative linkage, but not limited thereto, are targeting sequences for guaranteeing subcellular localization in the apoplasts, in the plasma membrane, in the vacuole, in plastids, into the mitochondrium, in the endoplasmatic reticulum (ER), in the nucleus, in liposomes or in other compartments and translation enhancers, such as the 5'-leader sequence from the tobacco mosaic virus (Gallie et al., Nucl. Acids Res. 15 (1987) 8693–8711).

Suitable promotors [sic] of the expression cassette according to the invention is, in principle, any promoter which is capable of governing the expression of foreign genes. Promoters which are preferably used are, in particular, a plant-derived promoter or a promoter originating from a plant virus. Particularly preferred is the CaMV 35S promotor from the cauliflower mosaic virus (Franck et al., Cell 21(1980) 285–294). This promoter contains various recognition sequences for transcriptional effectors, which, in their totality, lead to permanent and constitutive expression of the gene introduced (Benfey et al., EMBO J. 8 (1989) 2195–2202).

The expression cassette according to the invention may also comprise a chemically inducible promoter by means of which expression of the exogenous polypeptide in the plant can be controlled at a particular point in time. Such promoters, for example the PRP1 promoter (Ward et al., Plant.Mol.Biol.22(1993), 361–366), a promoter which is inducible by salicylic acid (WO 95/1919443), a promoter which is inducible by benzenesulfonamide (EP 388186), a promoter which is inducible by abscisic acid (EP335528) or a promoter which is inducible by ethanol or cyclohexanone (WO9321334), have been described in the literature and can be used, among others.

Other promoters which are particularly preferred are those which guarantee expression in tissues or plant organs in which the herbicidal activity takes place. Promoters which guarantee leaf-specific expression deserve particular mention. Mention must be made of the potato cytosolic FBPase promoter or the potato ST-LSI promoter (Stockhaus et al., EMBO J. 8 (1989) 2445–245).

The stable expression of single-chain antibodies, which amounted to up to 0.67% of the total soluble seed protein in the seeds of transgenic tobacco plants, was made possible with the aid of a seed-specific promoter (Fiedler and Conrad, Bio/Technology 10(1995), 1090–1094). Since expression may also be possible in seeds which have been sown or which are in the process of germination and may be desired for the purposes of the present invention, such germination- and seed-specific promoters are also regulatory elements which are preferred in accordance with the invention. Thus, the expression cassette according to the invention can therefore contain, for example, a seed-specific promoter (preferably the USP or LEB4 promotor), the LEB4 signal peptide, the gene to be expressed, and an ER retention signal. The construction of the cassette is shown by way of example in the form of a diagram in FIG. 1 with reference to a single-chain antibody (scFv gene).

An expression cassette according to the invention is produced by fusing a suitable promoter with a suitable polypeptide DNA and, preferably, a DNA which encodes a chloroplast-specific transit peptide and which is inserted between promoter and polypeptide DNA, and a polyadenylation signal, using customary recombination and cloning techniques as they are described, for example, in T. Maniatis, E. F. Fritsch and J. Sambrook, Molecular Cloning: A Laboratory manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

Particularly preferred are sequences which allow targeting into the apoplast, the plastids, the vacuole, into the plasma membrane, the mitochondrium, the endoplasmatic reticulum (ER) or, by the absence of suitable operative sequences, residence in the compartment of formation, namely the cytosol (Kermode, Crit. Rev. Plant Sci. 15, 4 (1996), 285–423). Localization in the ER and the cell wall have proved to be especially beneficial for quantitative protein accumulation in transgenic plants (Schouten et al. , Plant Mol. Biol. 30 (1996), 781–792; Artsaenko et al., Plant J. 8 (1995) 745–750).

The invention also relates to expression cassettes whose encoding sequence encodes a herbicide-binding fusion protein, part of the fusion protein being a transit peptide, which governs translocation of the polypeptide. Especially preferred are chloroplast-specific transit peptides which are cleaved enzymatically from the herbicide-binding polypeptide moiety after the herbicide-binding polypeptide has been translocated into the plant's chloroplasts. Particularly preferred is the transit peptide derived from plastid transketolase (TK) or a functional equivalent of this transit peptide (for example the transit peptide of the small subunit of Rubisco or ferredoxin NADP oxidoreductase).

The polypeptide DNA or polypeptide cDNA required for the production of expression cassettes according to the invention is preferably amplified with the aid of polymerase chain reaction (PCR). DNA amplification methods using PCR are known, for example from Innis et al., PCR Protocols, A Guide to Methods and Applications, Academic Press (1990). The PCR-produced DNA fragments can expediently be checked by sequence analysis to avoid polymerase errors in constructs to be expressed.

The nucleotide sequence inserted, which encodes a herbicide-binding polypeptide, can be generated synthetically or obtained naturally or comprise a mixture of synthetic and natural DNA components. In general, synthetic nucleotide sequences with codons which are preferred by plants are prepared. These codons which are preferred by plants can be determined from codons whose proteins are most frequent and which are expressed in most of the interesting plant species. When preparing an expression cassette, various DNA fragments can be manipulated so as to obtain a nucleotide sequence which expediently reads in the correct sense and which is equipped with a correct reading frame. To connect the DNA fragments to each other, adaptors or linkers can be added to the fragments.

The promoter and terminator regions according to the invention should expediently be provided, in the sense of the transcription, with a linker or polylinker comprising one or more restriction sites for insertion of this sequence. As a rule, the linker has 1 to 10, usually 1 to 8, preferably 2 to 6, restriction sites. Within the regulatory regions, the linker generally has a size of less than 100 bp, frequently less than 60 bp, but at least 5 bp. The promoter according to the invention can be either native or homologous or else foreign or heterologous to the host plant. The expression cassette according to the invention comprises, in the 5'-3'-sense of transcription, the promoter according to the invention, any desired sequence and a region for transcriptional termination. Various termination regions are mutually exchangeable as desired.

Furthermore, manipulations which provide suitable restriction sites or which remove excess DNA or restriction sites can be employed. Where insertions, deletions or substitutions, for example transitions and transversions, are possible, in-vitro mutagenesis, "primer repair", restriction or ligation may be used. In the case of suitable manipulations such as restriction, "chewing-back" or filling up projections for "blunt ends", complementary ends of the fragments may be provided for ligation purposes.

Especially important for the success according to the invention is the attachment of the specific ER retention signal SEKDEL (Schuoten, A. et al. Plant Mol. Biol. 30 (1996), 781–792), with which the average expression level is trebled to quadrupled. Other retention signals which occur naturally in plant and animal proteins which are localized in the ER may also be used for constructing the cassette.

Preferred polyadenylation signals are plant polyadenylation signals, preferably those which correspond essentially to T-DNA polyadenylation signals from Agrobacterium tumefaciens, in particular gene 3 of the T-DNA (octopin synthase) of the Ti plasmid pTiACH5 (Gielen et al., EMBO J. 3 (1984) 835 et seq.) or functional equivalents.

Figure 2:
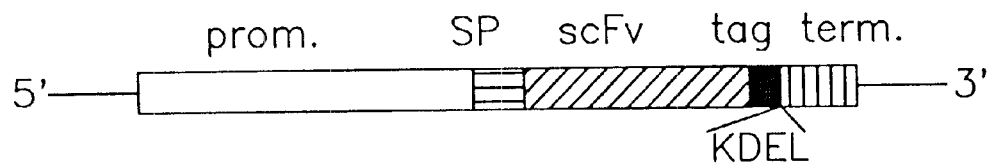

An expression cassette according to the invention may comprise, for example, a constitutive promotor (preferably the CaMV 35 S promotor), the LeB4 signal peptide, the gene to be expressed and the ER retention signal. The construction of the cassette is shown as a diagram in FIG. 2 with reference to a single-chain antibody (scFv gene). The amino-acid sequence KDEL (lysine, aspartic acid, glutamic acid, leucine) is preferably used as ER retention signal.

The fused expression cassette which encodes a polypeptide with herbicide-binding properties is preferably cloned into a vector, for example pBin19, which is suitable for transforming Agrobacterium tumefaciens. Agrobacteria which are transformed with such a vector can then be used in the known manner for transforming plants, in particular crop plants, eg. tobacco plants, by, for example, bathing wounded leaves or leaf sections in an Agrobacterial solution and subsequently growing them in suitable media. The transformation of plants by means of Agrobacteria is known, inter alia, from F. F. White, Vectors for Gene Transfer in Higher Plants; in Transgenic Plants, Vol. 1, Engineering and Utilization, edited by S. D. Kung and R. Wu, Academic Press, 1993, pp. 15–38, and from S. B. Gelvin, Molecular Genetics of T-DNA Transfer from Agrobacterium to Plants, also in Transgenic Plants, pp. 49–78. Transgenic plants can be regenerated from the transformed cells of the wounded leaves or leaf sections in the known manner, and these transgenic plants contain a gene for the expression of a polypeptide with herbicide-binding properties, integrated into the expression cassette according to the invention.

To transform a host plant with a DNA encoding a herbicide-binding polypeptide, an expression cassette according to the invention is incorporated, as an insertion, into a recombinant vector whose vector DNA contains additional functional regulation signals, for example sequences for replication or integration. Suitable vectors are described, inter alia, in "Methods in Plant Molecular Biology and Biotechnology" (CRC Press), (1993) chapter 6/7, pp.71–119.

Using the above-cited recombination and cloning techniques, the expression cassettes according to the invention can be cloned into suitable vectors which allow them to be multiplied, for example in E. coli. Suitable cloning vectors are, inter alia, pBR332, pUC series, M13mp series and pACYC184. Especially suitable are binary vectors which can replicate in both E. coli and agrobacteria, for example pBin19 (Bevan et al. (1980) Nucl. Acids Res. 12, 8711).

The invention furthermore relates to the use of an expression cassette according to the invention for the transformation of plants, plant cells, plant tissues or plant organs. The preferred aim upon use is the mediation of resistance to plant-enzyme inhibitors.

Depending on the choice of the promoter, expression can take place specifically in the leaves, in the seeds or in other plant organs. Such transgenic plants, their propagation material and their plant cells, plant tissues or plant organs are a further subject of the present invention.

The transfer of foreign genes into the genome of a plant is termed transformation. In this process, the above-described methods of transforming and regenerating plants from plant tissues or plant cells are utilized for transient or stable transformation. Suitable methods are protoplast transformation by polyethylene glycol-induced DNA uptake, the biolistic [sic] approach using the gene gun, electroporation, incubation of dry embryos in DNA-containing solution, microinjection and Agrobacterium-mediated gene transfer. The methods mentioned are described, for example, in B. Jenes et al., Techniques for Gene Transfer, in: Transgenic Plants, Vol. 1, Engineering and Utilization, editors: S. D. Kung and R. Wu, Academic Press (1993) 128–143 and in Potrykus, Annu.Rev.Plant Physiol.Plant Molec.Biol. 42 (1991) 205–225). The construct to be expressed is preferably cloned into a vector which is suitable for the transformation of *Agrobacterium tumefaciens*, for example pBin19 (Bevan et al., Nucl. Acids Res. 12 (1984) 8711).

Agrobacteria which have been transformed with an expression cassette according to the invention can then be used in the known manner for transforming plants, in particular crop plants such as cereals, maize, soya, rice, cotton, sugar beet, canola, sunflower, flax, potato, tobacco, tomato, oilseed rape, alfalfa, lettuce and the various tree, nut and Vitis species, for example by bathing wounded leaves or leaf sections in an agrobacterial solution and subsequently growing them in suitable media.

Functionally equivalent sequences which encode a herbicide-binding polypeptide are, in accordance with the invention, those sequences which still have the desired functions, despite a different nucleotide sequence. Thus, functional equivalents encompass naturally occurring variants of the sequences described herein, and also artificial nucleotide sequences, for example artificial nucleotide sequences which have been obtained by chemical synthesis and are adapted to the codon usage of a plant.

In particular, functional equivalent is to be understood as a natural or artificial mutation of an originally isolated sequence which encodes the herbicide-binding polypeptide, which mutation continues to show the desired function. Mutations encompass substitutions, additions, deletions, exchanges or insertions of one or more nucleotide residues. Thus, the present invention also encompasses those nucleotide sequences which are obtained by modifying this nucleotide sequence. The purpose of such a modification can be, for example, the further limitation of the encoding sequence contained therein, or else, for example, the insertion of more cleavage sites for restriction enzymes.

Other functional equivalents are those variants whose function is less or more pronounced, in comparison with the starting gene or gene fragment.

Moreover, artificial DNA sequences are suitable as long as they induce the desired resistance to herbicides, as described above. Such artificial DNA sequences can be identified, for example, by backtranslating proteins which have herbicide-binding activity and which have been constructed by means of molecular modeling, or by in vitro selection. Especially suitable are encoding DNA sequences which have been obtained by backtranslating a polypeptide sequence in accordance with the codon utilization which is specific to the host plant. The specific codon utilization can be determined readily by an expert familiar with methods of plant genetics by computer-aided evaluation of other, known genes of the plant to be transformed.

Further suitable equivalent nucleic acid sequences according to the invention which must be mentioned are sequences which encode fusion proteins, where part of the fusion protein is a non-plant-derived herbicide-binding polypeptide or a functionally equivalent part thereof. For example, the second part of the fusion protein can be a further polypeptide with enzymatic activity, or an antigenic polypeptide sequence with the aid of which detection of scFvs expression is possible (for example myc-tag or his-tag). However, it is preferably a regulatory protein sequence, for example a signal or transit peptide, which directs the polypeptide with herbicide-binding properties to the desired site of action.

However, the invention also relates to the expression products produced in accordance with the invention and to fusion proteins of a transit peptide and a polypeptide with herbicide-binding properties.

Resistance/tolerance means, for the purposes of the present invention, the artificially acquired ability of plants to withstand the action of plant enzyme inhibitors. It embraces the partial and, in particular, complete insensitivity to these inhibitors for the duration of at least one plant generation.

The primary site of action of herbicides is generally the leaf tissue, so that leaf-specific expression of the exogenous herbicide-binding polypeptide is capable of providing sufficient protection. However, one will understand readily that the action of a herbicide need not be restricted to the leaf tissue, but may also be effected in all remaining organs of the plant in a tissue-specific manner.

In addition, constitutive expression of the exogenous herbicide-binding polypeptide is advantageous. On the other hand, inducible expression may also be desirable.

The efficacy of the transgenically expressed polypeptide with herbicide-binding properties can be determined for example in vitro by shoot meristem propagation on herbicide-containing medium in series with staggered concentrations, or via seed germination tests. In addition, the herbicide tolerance, of a test plant, which has been altered with regard to type and level can be tested in greenhouse experiments.

The invention furthermore relates to transgenic plants, transformed with an expression cassette according to the invention, and to transgenic cells, tissues, organs and propagation material of such plants. Especially preferred are transgenic crop plants, for example cereals, maize, soya, rice, cotton, sugar beet, canola, sunflower, flax, potato, tobacco, tomato, oilseed rape, alfalfa, lettuce and the various tree, nut and Vitis species.

The transgenic plants, plant cells, plant tissues or plant organs can be treated with an active ingredient which inhibits the plant enzymes, whereby the plants, plant cells, plant tissues or plant organs which have not been transformed successfully die. Examples of suitable active ingredients are in particular 5-(2-chloro-4-(trifluoromethyl) phenoxy)-2-nitrobenzoic acid (acifluorfen) and 7-chloro-3-methylquinolin-8-carboxylic acid (quinmerac), and metabolites and functional derivatives of these compounds. The DNA which encodes a polypeptide with herbicide-binding properties and which has been inserted into the expression cassettes according to the invention can thus also be used as selection marker.

The present invention has the advantage, in particular in the case of crop plants, that, once a selected resistance of the crop plant to the plant enzyme inhibitors has been induced, such inhibitors can be employed as specific herbicides to the non-resistant plants. Herbicidal compounds from the groups bl-641 may be mentioned as examples of such inhibitors, but not by way of limitation:

b1 1,3,4-Thiadiazoles:
  buthidazole, cyprazole
b2 Amides:
  allidochlor (CDAA), benzoylprop-ethyl, bromobutide, chlorthiamid, dimepiperate, dimethenamid, diphenamid, etobenzanid (benzchlomet), flamprop-methyl, fosamin, isoxaben, monalide, naptalame, pronamid (propyzamid), propanil
b3 Aminophosphoric acids:
  bilanafos, (bialaphos), buminafos, glufosinate-ammonium, glyphosate, sulfosate
b4 Aminotriazoles:
  amitrole
b5 Anilides:
  anilofos, mefenacet
b6 Aryloxyalkanoic acids:
  2,4-D, 2,4-DB, clomeprop, dichlorprop, dichlorprop-P, dichlorprop-P (2,4-DP-P), fenoprop (2,4,5-TP), fluoroxypyr, MCPA, MCPB, mecoprop, mecoprop-P, napropamide, napropanilide, triclopyr
b7 Benzoic acids:
  chloramben, dicamba
b8 Benzothiadiazinones:
  bentazone
b9 Bleachers:
  clomazone (dimethazone), diflufenican, fluorochloridone, flupoxam, fluridone, pyrazolate, sulcotrione (chlormesulone)
b10 Carbamates:
  asulam, barban, butylate, carbetamid, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate, vernolate
b11 Quinoline acids:
  quinclorac, quinmerac
b12 Chloroacetanilides:
  acetochlor, alachlor, butachlor, butenachlor, diethatylethyl, dimethachlor, metazachlor, metolachlor, pretilachlor, propachlor, prynachlor, terbuchlor, thenylchlor, xylachlor
b13 Cyclohexenones:
  alloxydim, caloxydim, clethodim, cloproxydim, cycloxydim, sethoxydim, tralkoxydim, 2-{1-[2-(4-chlorophenoxy)propyloxyimino]butyl}-3-hydroxy-5-(2H-tetrahydrothiopyran-3-yl)-2-cyclohexen-1-one
b14 Dichloropropionic acids:
  dalapon
b15 Dihydrobenzofurans:
  ethofumesate
b16 Dihydrofuran-3-ones:
  flurtamone b17 Dinitroanilines:
  benefin, butralin, dinitramin, ethalfluralin, fluchloralin, isopropalin, nitralin, oryzalin, pendimethalin, prodiamine, profluralin, trifluralin
b18 Dinitrophenols:
  bromofenoxim, dinoseb, dinoseb-acetate, dinoterb, DNOC
b19 Diphenyl ethers:
  acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen
b20 Dipyridylenes:
  cyperquat, difenzoquat-methylsulfate, diquat, paraquat dichlorid
b21 Ureas:
  benzthiazuron, buturon, chlorbromuron, chloroxuron, chlortoluron, cumyluron, dibenzyluron, cycluron, dimefuron, diuron, dymrone, ethidimuron, fenuron, fluormeturon, isoproturon, isouron, karbutilate, linuron, methabenzthiazuron, metobenzuron, metoxuron, monolinuron, monuron, neburon, siduron, tebuthiuron, trimeturon
b22 Imidazoles:
  isocarbamid
b23 Imidazolinones:
  imazamethapyr, imazapyr, imazaquin, imazethabenz-methyl (imazame), imazethapyr
b24 Oxadiazoles:
  methazole, oxadiargyl, oxadiazon
b25 Oxiranes:
  tridiphane
b26 Phenols:
  bromoxynil, ioxynil
b27 Phenoxyphenoxypropionic esters:
  clodinafop, cyhalofop-butyl, diclofop-methyl, fenoxapropethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofopethyl, quizalofop-p-ethyl, quizalofop-tefuryl
b28 Phenylacetic acids:
  chlorfenac (fenac)
b29 Phenylpropionic acids:
  chlorophenprop-methyl
b30 Protoporphyrinogen IX oxydase inhibitors:
  benzofenap, cinidon-ethyl, flumiclorac-pentyl, flumioxazin, flumipropyn, flupropacil, fluthiacet-methyl, pyrazoxyfen, sulfentrazone, thidiazimin
b31 Pyrazoles:
  nipyraclofen
b32 Pyridazines:
  chloridazon, maleic hydrazide, norflurazon, pyridate
b33 Pyridinecarboxylic acids:
  clopyralid, dithiopyr, picloram, thiazopyr
b34 Pyrimidyl ethers:
  pyrithiobac-acid, pyrithiobac-sodium, KIH-2023, KIH-6127
b35 Sulfonamides:
  flumetsulam, metosulam
b36 Sulfonylureas:
  amidosulfuron, azimsulfuron, bensulfuron-methyl, chlorimuronethyl, chlorsulfuron, cinosulfuron, cyclosulfamuron, ethametsulfuron-methyl, ethoxysulfuron, flazasulfuron, halosulfuronmethyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl
b37 Triazines:
  ametryn, atrazine, aziprotryn, cyanazine, cyprazine, desmetryn, dimethamethryn, dipropetryn, eglinazine-ethyl, hexazinone, procyazine, prometon, prometryn, propazine, secbumeton, simazine, simetryn, terbumeton, terbutryn, terbutylazine, trietazine
b38 Triazinones:
  ethiozin, metamitron, metribuzin
b39 Triazolecarboxamides:
  triazofenamid
b40 Uraciles
  bromacil, lenacil, terbacil
b4Others:
  benazolin, benfuresate, bensulide, benzofluor, butamifos, cafenstrole, chlorthal-dimethyl (DCPA), cinmethylin, dichlobenil, endothall, fluorbentranil, mefluidide, perfluidone, piperophos The spectrum of action of functionally equivalent derivatives of plant enzyme inhibitors is comparable with the spectrum of action of the substances named individually, while the inhibitory activity (for example expressed in g of inhibitor per hectare under cultivation, required for completely suppressing the growth of non-resistent plants) is lower, identical or higher.

The invention is now illustrated by the examples which follow, but is not limited thereto:

General Cloning Methods

The cloning steps carried out within the scope of the present invention, for example restriction cleavages, agarose gel electrophoresis, purification of DNA fragments, transfer of nucleic acids to nitrocellulose and nylon membranes, linkage of DNA fragments, transformation of *E. coli* cells, cultivation of bacteria, multiplication of phages and sequence analysis of recombinant DNA were carried out as described by Sambrook et al. (1989) Cold Spring Harbor Laboratory Press; ISBN 0-87969-309-6).

The bacterial strains used hereinbelow (*E. coli*, XL-I Blue) were obtained from Stratagene. The agrobacterial strain used for the transformation of plants (*Agrobacterium tumefaciens*, C58C1 with plasmid pGV2260 or pGV3850kan) was described by Deblaere et al. (Nucl. Acids Res. 13 (1985) 4777). Alternatively, the agrobacterial strain LBA4404 (Clontech) or other suitable strains may also be used. The vectors pUC19 (Yanish-Perron, Gene 33(1985), 103–119) pBluescript SK-(Stratagene), pGEM-T (Promega), pZerO (Invitrogen), pBin19 (Bevan et al., Nucl. Acids Res. 12(1984) 8711–8720) and pBinAR (Höfgen and Willmitzer, Plant Science 66 (1990) 221–230) were employed for cloning purposes.

Sequence Analysis of Recombinant DNA

Recombinant DNA molecules were sequenced using a laser fluorescence DNA sequencing apparatus from Pharmacia, using the method of Sanger (Sanger et al., Proc. Natl. Acad. Sci. USA 74(1977), 5463–5467).

Generation of Plant Expression Cassettes

A 35S CaMV promoter was inserted into plasmid pBin19 (Bevan et al., Nucl. Acids Res. 12, 8711 (1984)) in the form of an EcoRI-KpnI fragment (corresponding to nucleotides 6909–7437 of the cauliflower mosaic virus (Franck et al. Cell 21 (1980) 285). The polyadenylation signal of gene 3 of the T-DNA of the Ti plasmid pTiACH5 (Gielen et al., EMBO J. 3 (1984) 835), nucleotides 11749–11939, was isolated in the form of a PvuII-HindIII fragment and, after SphI linkers had been added, cloned into the PvuII cleavage site between the SphI-HindIII cleavage site of the vector. This gave plasmid pBinAR (Höfgen and Willmitzer, Plant Science 66 (1990) 221–230).

USE EXAMPLES

Example 1

Since herbicides are not immunogenic, they must be coupled to a carrier material, for example KLH. If the molecule contains a reactive group, coupling may be effected directly; if not, a functional group is introduced when the herbicide is synthesized or a reactive precursor is selected during synthesis so as to couple these molecules to the carrier molecule in a simple reaction step. Examples of coupling reactions can be found in Miroslavic Ferencik in "Handbook of Immunochemistry", 1993, Chapman & Hall, in the chapter Antigens, pages 20–49.

Repeated injection of this modified carrier molecule (antigen) is used for immunizing, for example, Balb/c mice. Once a sufficient number of antibodies with binding to the antigen is detectable in the ELISA (enzyme-linked immunosorbent assay), the spleen cells of these animals are removed and fused with myeloma cells in order to cultivate hybrids. "Herbicide-modified BSA" is additionally used as antigen in the ELISA so as to differentiate the immune response directed against the hapten from the KLH response.

Monoclonal antibodies are prepared by methods similar to known methods, for example as described in "Practical Immunology", Leslie Hudson and Frank Hay, Blackwell Scientific Publications, 1989 or in "Monoclonal Antibodies: Principles and Practice", James Goding, 1983, Academic Press, Inc., or in "A practical guide to monoclonal antibodies", J.Liddell and A. Cryer,1991, John Wiley& Sons; or Achim Möller and Franz Emling "Monoklonale Antikörper gegen TNF und deren Verwendung" [Monoclonal antibodies against TNF, and their use]. European Patent Specification EP-A260610.

Example 2

The starting point of the investigation was a monoclonal antibody which specifically recognizes the herbicide quinmerac and which, additionally, has a high binding affinity. The hydridoma cell line selected is characterized in that the secreted monoclonal antibodies which are directed against the herbicide antigen quinmerac have a high affinity and the specific sequences of the immunoglobulins are available (Berek, C. et al., Nature 316, (1985) 412–418). This monoclonal antibody against quinmerac was the starting point for the construction of the single-chain antibody fragment (scFv-antiquinmerac).

Figure 3:
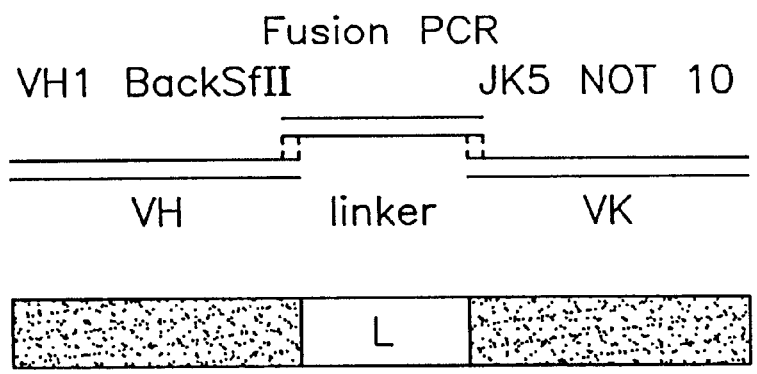

First, mRNA was isolated from the hybridoma cells and transcribed into cDNA. This cDNA acted as a template for the amplification of the variable immunglobulin genes VH and VK with the specific primers VH1 BACK and VH FOR-2 for the heavy chain and VK2 BACK and MJK5 FON X for the light chain (Clackson et al., Nature 352, (1991) 624–628). The variable immunoglobulins isolated were the starting point for the construction of a single-chain antibody fragment (scFv-antiquinmerac). In the subsequent fusion PCR, three components VH,VK and a linker fragment were combined in a PCR reaction, and the scFv-antiquinmerac was amplified (FIG. 3).

Figure 4:
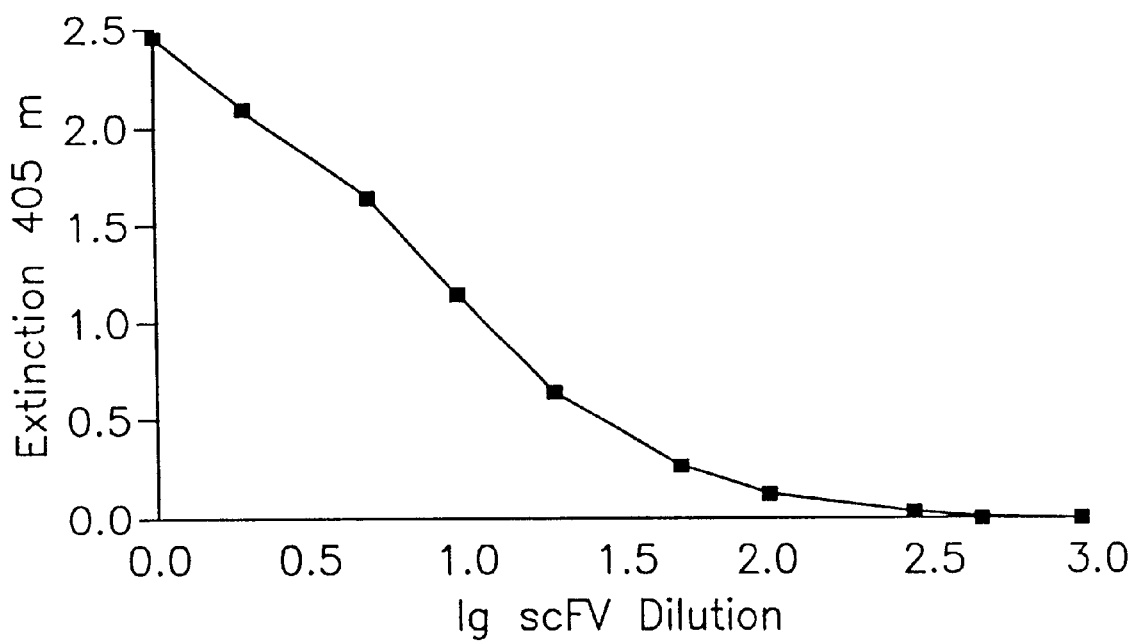

Functional characterization (antigen binding activity) of the scFv-antiquinmerac gene constructed was carried out after expression in a bacterial system. To this end, the scFv-antiquinmerac was synthesized in *E. coli* as a soluble antibody fragment, using the method of Hoogenboom, H. R. et al., Nucleic Acids Research, 19, (1991) 4133–4137. Activity and specificity of the antibody fragment constructed were checked in an ELISA assay (FIG. 4).

Figure 5:
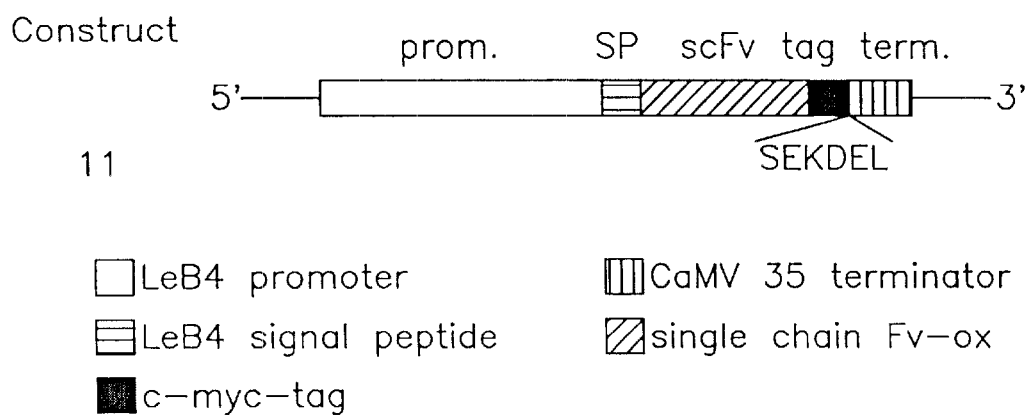

To allow seed-specific expression of the antibody fragment in tobacco, the scFv-antiquinmerac gene was cloned downstream from the LeB4 promoter. The LeB4 promoter, which had been isolated from *Vicia faba*, shows strictly seed-specific expression of various foreign genes in tobacco (Bäumlein, H. et al., Mol. Gen. Genet. 225, (1991) 121–128). Transport of the scFv-antiquinmerac polypeptide into the endoplasmatic reticulum resulted in stable accumulation of large amounts of antibody fragment. To this end, the scFv-antiquinmerac gene was fused with a signal peptide sequence which guarantees entry into the endoplasmatic reticulum and with the ER retention signal SEKDEL, which guarantees that the polypeptide remains in the ER (Wandelt et al.,1992) (FIG. 5).

The expression cassette constructed was cloned into the binary vector pGSGLUC 1 (Saito et al., 1990) and transferred into the agrobacterium strain EHA 101 by electroporation. Recombinant agrobacterial clones were used for the subsequent transformation of *Nicotiana tabacum*. 70–140 tobacco plants were regenerated per construct. Seeds in different developmental stages were harvested from the regenerated transgenic tobacco plants, following self-pollination. The soluble proteins were obtained from these seeds in an aqueous buffer system, after extraction. Analysis of the transgenic plants demonstrates that fusion of the scFv-antiquinmerac gene to the DNA sequence of the ER retention signal SEKDEL allowed a maximum accumulation of 1.9% scFv-antiquinmerac protein to be obtained in the mature seed.

The scFv-antiquinmerac gene constructed had a size of approximately 735 bp. The variable domains were fused to each other in the sequence VH-L-VL.

The specific selectivity was determined in the extracts of the mature tobacco seeds using a direct ELISA. The values obtained demonstrate clearly that the protein extracts contain functionally active antibody fragments.

Example 3

Seed-specific expression and concentration of single-chain antibody fragments in the endoplasmatic reticulum of cells of transgenic tobacco seeds, under the control of the USP promoter.

Starting point of the investigations was a single-chain antibody fragment against the herbicide quinmerac (scFv-antiquinmerac). The functional characterization (antigen binding activity) of this scFv-antiquinmerac gene constructed was carried out following expression in a bacterial system and following expression in tobacco leaves. Activity and specificity of the antibody fragment constructed were checked with ELISA assays.

To allow seed-specific expression of the antibody fragment in tobacco, the scFv-antiquinmerac gene was cloned downstream from the USP promoter. The USP promoter, which had been isolated from *Vicia faba*, shows strictly seed-specific expression of various foreign genes in tobacco (Fiedler, U. et al., Plant Mol. Biol. 22, (1993) 669–679). Transport of the scFv-antiquinmerac polypeptide into the endoplasmatic reticulum resulted in stable accumulation of large amounts of antibody fragment. To this end, the scFv-antiquinmerac gene was fused with a signal peptide sequence which guarantees entry into the endoplasmatic reticulum and with the ER retention signal SEKDEL, which guarantees that the polypeptide remains in the ER (Wandelt et al., 1992) (FIG. 1).

The expression cassette constructed was cloned into the binary vector pGSGLUC 1 (Saito et al., 1990) and transferred into the Agrobacterium strain EHA 101 by electroporation. Recombinant agrobacterial clones were used for the subsequent transformation of Nicotiana tabacum. Seeds in different developmental stages were harvested from the regenerated transgenic tobacco plants, following self-pollination. The soluble proteins were obtained from these seeds in an aqueous buffer system, after extraction. Analysis of the transgenic plants demonstrates that fusion of the scFv-antiacifluorfen [sic] gene to the DNA sequence of the ER retention signal SEKDEL under the control of the USP promoter caused single-chain antibody fragments with a binding affinity for quinmerac to be synthesized as early as day 10 of the seed development.

Example 4

To achieve ubiquitous expression of the antibody fragment in the plant, especially in leaves, the scFv-antiquinmerac gene was cloned downstream of the CaMV 35 S promoter. This strong constitutive promoter mediates expression of foreign genes in virtually all plant tissues (Benfey and Chua, Science 250 (1990), 956–966. Transport of the scFv-antiquinmerac protein into the endoplasmatic reticulum allowed stable accumulation of large amounts of antibody fragment to be obtained in the leaf material. First, the scFv-antiquinmerac gene was fused to a signal peptide sequence which ensures entry into the endoplasmatic reticulum and to the ER retention signal KDEL, which ensures that the product remains in the ER (Wandelt et al., Plant J. 2(1992), 181–192). The expression cassette constructed was cloned into the binary vector pGSGLUC 1 (Saito et al., Plant Cell Rep. 8(1990), 718–721) and transferred into the Agrobacterium strain EHA 101 by electroporation. Recombinant agrobacterial clones were used for the subsequent transformation of Nicotiana tabacum. Approximately 100 tobacco plants were regenerated. Leaf material of various developmental stages was removed from the regenerated transgenic tobacco plants. The soluble proteins were obtained from this leaf material in an aqueous buffer system, following extraction. Subsequent analyses (western blot analyses and ELISA assays) demonstrated that a maximum accumulation of more than 2% of biologically active antigen-binding scFv-antiquinmerac polypeptide was obtained in the leaves. The high expression values were determined in fully grown green leaves, but the antibody fragment was also detected in senescent leaf material.

Example 5

PCR amplification of a fragment of the cDNA encoding the single-chain antibody against acifluorfen and quinmerac with the aid of synthetic oligonucleotides.

The PCR amplification of the single-chain antibody cDNA was carried out in a DNA thermal cycler from Perkin Elmer. The reaction mixtures contained 8 ng/µl single-stranded template cDNA, 0.5 µM of the relevant oligonucleotides, 200 µM nucleotides (Pharmacia), 50 mM KCl, 10 mM Tris-HCl (pH 8.3 at 25° C., 1.5 mM MgCl$_2$) and 0.02 U/µl Taq polymerase (Perkin Elmer). The amplification conditions were set as follows:

| Annealing temperature: | 45° C., |
|---|---|
| Denaturation temperature: | 94° C., |
| Elongation temperature: | 72° C., |
| Number of cycles: | 40 |

The result is a fragment of approx. 735 base pairs, which was ligated into the vector pBluescript. The ligation mixture was used for transforming E. coli XL-I Blue, and the plasmid was amplified. Regarding use and optimization of polymerase chain reaction, see: Innis et al., 1990, PCR Protocols, A Guide to Methods and Applications, Academic Press.

Example 6

Production of transgenic tobacco plants which express a cDNA encoding a single-chain antibody with herbicide-binding properties.

Plasmid pGSGLUC 1 was transformed into Agrobacterium tumefaciens C58C1:pGV2260. To transform tobacco plants (Nicotiana tabacum cv. Samsun NN), a 1:50 dilution of an overnight culture of a positively transformed agrobacterial colony in Murashige-Skoog medium (Physiol. Plant. 15 (1962) 473 et seq.) containing 2% of sucrose (2MS medium) was used. In a Petri dish, leaf disks of sterile plants (each approx. 1 cm$^2$) were incubated for 5–10 minutes in a 1:50 agrobacterial dilution. This is followed by 2 days' incubation in the dark at 25° C. on 2MS medium containing 0.8% Bacto-Agar. Cultivation was continued after 2 days in 16 hours light/8 hours dark and continued in a weekly rhythm on MS medium containing 500 mg/l Claforan (cefotaxim-sodium), 50 mg/l kanamycin, 1 mg/l benzylaminopurine (BAP), 0.2 mg/l naphthylacetic acid and 1.6 g/l glucose. Growing shoots were transferred to MS medium containing 2% sucrose, 250 mg/l Claforan and 0.8% Bacto-Agar.

Example 7

Stable accumulation of the single-chain antibody fragment against the herbicide quinmerac in the endoplasmatic reticulum.

Starting point of the investigations was a single-chain antibody fragment against the herbicide quinmerac(scFv-antiquinmerac) which is expressed in tobacco plants. Quantity and activity of the scFv-antiquinmerac polypeptide synthesized were determined in western blot analyses and ELISA assays.

Figures 6A, 6B:
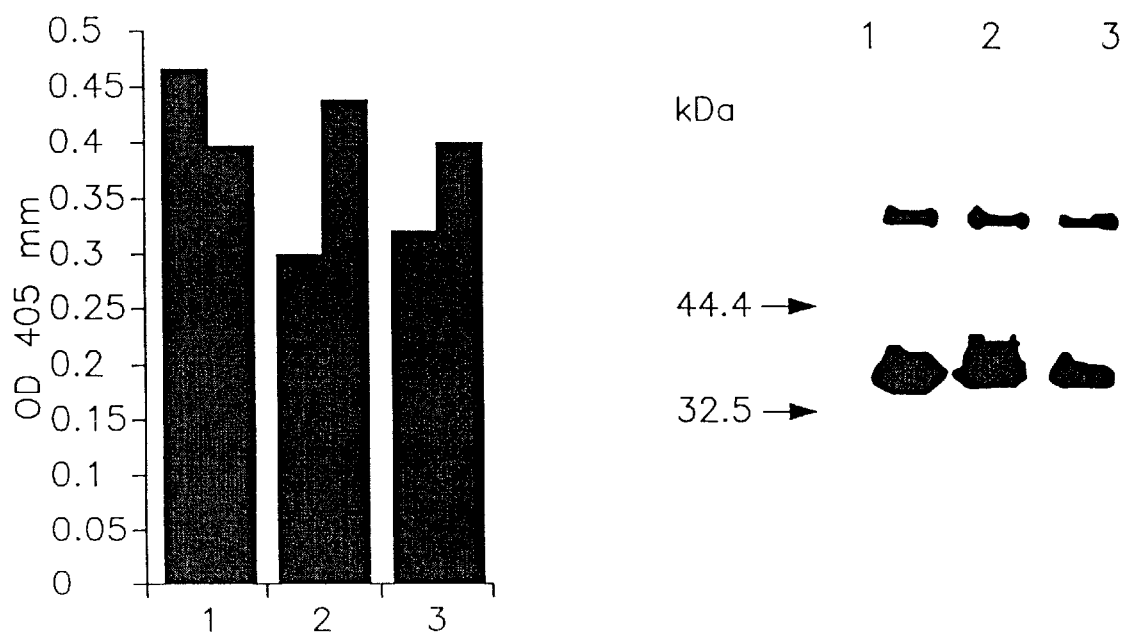

To make possible expression of the scFv-antiquinmerac gene in the endoplasmatic reticulum, the foreign gene was expressed under the control of the CaMV 53S promoter as a translation fusion with the LeB4 signal peptide (N-terminal) and the ER retention signal KDEL (C-terminal). Transport of the scFv-antiquinmerac polypeptide into the endoplasmatic reticulum allowed stable accumulation of large quantities of active antibody fragment. After the leaf material had been harvested, sections were frozen at −20° C. (1), lyophilized (2) or dried at room temperature (3). The soluble proteins were obtained from the leaf material in question by extraction in an aqueous buffer, and the scFv-antiquinmerac polpypeptide was purified by affinity chromatography. Equal amounts of purified scFv-antiquinmerac polypeptide (frozen, lyophilized and dried) were employed for determining the activity of the antibody fragment (FIG. 6). FIG. 6A shows antigen binding activity of the scFv-antiquinmerac polypeptide from fresh (1), lyophilized (2) and dried (3) leaves. FIG. 6B shows the respective amounts of scFv-antiquinmerac protein (approximately 100 ng), used for the ELISA analyses, determined by western blot analyses. The sizes of the protein molecular weight standards are shown on the left. Approximately identical antigen binding activities were found.

Example 8

To demonstrate the herbicide tolerance of the transgenic tobacco plants which produce a polypeptide with herbicide-binding properties, these tobacco plants were treated with various amounts of acifluorfen and quinmerac. It was possible to demonstrate in all cases, in the greenhouse, that the plants expressing an scFv-antiacifluorfen and scFv-antiquinmerac, respectively, showed tolerance to the herbicides in question in comparison with the control.

sequence, a gene encoding an 5-(2-chloro-4-(trifluoromethyl)phenoxy)-2-nitrobenzoic acid or 7-chloro-3-methylIquinoline-8-carboxylic acid binding antibody, and a terminator.

11. The expression cassette as claimed in claim 10, wherein said promoter is the CaMV 35S promoter.

12. The expression cassette as claimed in claim 10, wherein said gene encodes a single-chain antibody.

13. The expression cassette as claimed in claim 10, wherein the gene encoding a 5-(2-chloro-4-(trifluoromethyl)phenoxy)-2-nitrobenzoic acid or 7-chloro-3-methylIquinoline-8-carboxylic acid-binding antibody is in the form of a translation fusion with a gene encoding another functional protein or is employed as the gene to be expressed.

14. The expression cassette as claimed in claim 10, wherein an antibody gene to be expressed is isolated from a hybridoma cell or phage display libraries.

15. A process of transforming dicotyledonous or monocotyledonous plants comprising the step of introducing the expression cassette as claimed in claim 10 into the plant genome, wherein the 5-(2-chloro-4-(trifluoromethyl)

---

---

We claim:

1. A process for the production of a 5-(2-chloro-4-(trifluoromethyl)phenoxy)-2-nitrobenzoic acid or 7-chloro-3-methylIquinoline-8-carboxylic acid tolerant plant, said process comprising the step of transforming plants to produce an exogenous 5-(2-chloro-4-(trifluoromethyl)phenoxy)-2-nitrobenzoic acid or 7-chloro-3-methylIquinoline-8-carboxylic-binding antibody in the plants, and selecting a tolerant plant.

2. The process as claimed in claim 1, wherein the exogenous antibody is a single-chain antibody binding fragment.

3. The process as claimed in claim 1, wherein the exogenous antibody is a complete antibody or a binding fragment.

4. The process as claimed in claim 1, wherein the plant is mono- or dicotyledonous.

5. The process as claimed in claim 4, wherein the plant is tobacco.

6. The process as claimed in claim 1, wherein the antibody is expressed constitutively in the plant.

7. The process as claimed in claim 1, wherein expression of the exogenous antibody in the plant is induced.

8. The process as claimed in claim 1, wherein the exogenous antibody is expressed in the leaves of the plant.

9. The process as claimed in claim 1, wherein the exogenous antibody is expressed in the seeds of the plant.

10. An expression cassette for plants, comprising in operative linkage a plant-functional promoter, a targeting phenoxy)-2-nitrobenzoic acid or 7-chloro-3-methylIquinoline-8-carboxylic acid-binding antibody is expressed seed- or leaf specifically.

16. The process as claimed in claim 15, wherein the expression cassette is first transferred into a bacterial strain and resulting recombinant transformed bacterial clones are used for the transformation of the dicotyledonous or monocotyledonous plants to express a 5-(2-chloro-4-(trifluoromethyl)phenoxy)-2-nitrobenzoic acid or 7-chloro-3-methylIquinoline-8-carboxylic-binding antibody seed- or leaf- specifically.

17. A process for the transformation of a plant, the said process comprising the step of introducing a gene sequence which encodes a 5-(2-chloro-4-(trifluoromethyl)phenoxy)-2-nitrobenzoic acid or 7-chloro-3-methylIquinoline-8-carboxylic acid-binding antibody into a plant cell, into callus tissue, into an entire plant or into protoplasts.

18. The process as claimed in claim 17, wherein introduction is performed by agrobacterium.

19. The process as claimed in claim 17, wherein introduction is performed by electroporation.

20. The process as claimed in claim 17, wherein introduction is by a particle bombardment method.

21. A method of producing a 5-(2-chloro-4-(trifluoromethyl)phenoxy)-2-nitrobenzoic acid or 7-chloro-3-methylIquinoline-8-carboxylic acid-binding antibody, said method comprising the step of introducing into a plant genome and expressing a gene which encodes said antibody in a plant or cells of a plant, and subsequently isolating the antibody.

22. A plant comprising the expression cassette as claimed in claim 10, wherein the expression cassette imparts tolerance to 5-(2-chloro-4-(trifluoromethyl)phenoxy)-2-nitrobenzoic acid or 7-chloro-3-methyllquinoline-8-carboxylic acid.

23. The process as claimed claim 18, wherein the agrobacterium is *Agrobacteium tumefaciens*.

24. A process for selecting transformed plant cells, said process comprising the step of transforming cells with the expression cassette as claimed in claim 10, and culturing said transformed plant cells in the presence of herbicides.

* * * * *

UNITED STATES PATENT AND TRADEMARK OFFICE
CERTIFICATE OF CORRECTION

PATENT NO. : 6,472,587 B1  Page 1 of 1
DATED : October 29, 2002
INVENTOR(S) : Lerchl et al.

It is certified that error appears in the above-identified patent and that said Letters Patent is hereby corrected as shown below:

Title page, Item [54] and Column 1, lines 1-10,
Cancel the title printed on the patent and substitute: -- EXPRESSION OF HERBICIDE-BINDING POLYPEPTIDES IN PLANTS TO PRODUCE HERBICIDE TOLERANCE --.

Column 17,
Lines 44 and 48, "methyllquinoline" should be -- methylquinoline --

Column 18,
Lines 3, 12, 42, 49, 53 and 63, "methyllquinoline" should be -- methylquinoline --

Column 19,
Lines 4, "methyllquinoline" should be -- methylquinoline --

Signed and Sealed this

Eighteenth Day of February, 2003

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 6
<212> TYPE: PRT
<213> ORGANISM: Unknown
<220> FEATURE:
<223> OTHER INFORMATION: Endoplasmic reticulum retention signal

<400> SEQUENCE: 1

Ser Glu Lys Asp Glu Leu
1               5